United States Patent [19]

Dille et al.

[11] 4,045,671
[45] Aug. 30, 1977

[54] METHOD AND APPARATUS FOR CONTINUOUSLY MONITORING THE PRESENCE OF OIL IN WATER

[75] Inventors: Roger M. Dille; Merle H. Van Stavern, both of Richmond; Don L. Shull, Waynesboro; David F. Gripshover, Richmond, all of Va.

[73] Assignee: Texaco Inc., New York, N.Y.

[21] Appl. No.: 636,174

[22] Filed: Nov. 28, 1975

[51] Int. Cl.² ............................................. G01N 21/26
[52] U.S. Cl. ..................................... 250/341; 250/343
[58] Field of Search ............... 250/343, 344, 345, 346, 250/340, 341; 356/70

[56] References Cited

U.S. PATENT DOCUMENTS 3,627,419  12/1971  Thevenier ............................ 356/70
3,727,049  4/1973  Saunders ............................. 250/343

*Primary Examiner*—Craig E. Church
*Attorney, Agent, or Firm*—Thomas H. Whaley; Carl G. Ries; Henry C. Dearborn

[57] ABSTRACT

A sensitive arrangement for determining presence of oil, at low parts per million, in water. It employs infrared absorbtion measurement, and first mixes the water with an oil solvent that may be separated from the water after taking any oil into solution. Also, the solvent is one which does not have any significant infrared absorbency at a predetermined wave length, which does have absorbency by hydrocarbons. After separation of the oil solvent, it is continuously passed through an absorption cell in an infrared spectrometer, to monitor the presence of oil in the water.

8 Claims, 1 Drawing Figure

U.S. Patent  Aug. 30, 1977  4,045,671
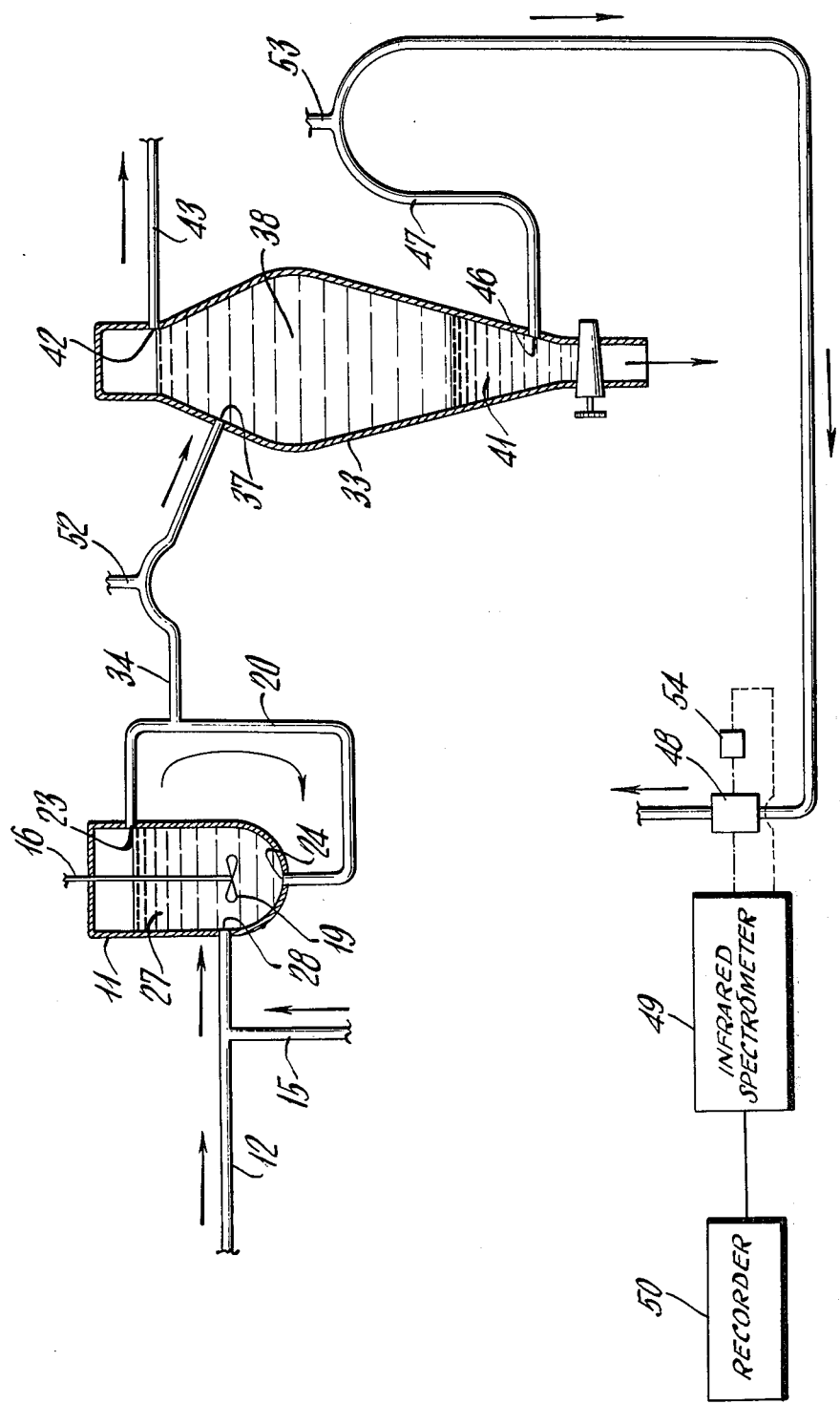

4,045,671

METHOD AND APPARATUS FOR CONTINUOUSLY MONITORING THE PRESENCE OF OIL IN WATER

BACKGROUND OF THE INVENTION

1. Field of the Invention

This invention is concerned with the detection of oil in water. More specifically, it deals with a method and apparatus for continuously monitoring the presence of oil in water 2. Description of the Prior Art Heretofor it has been known that there are numerous procedures for measuring and/or detecting the presence of oil in water. However, such procedures had various drawbacks, depending in part upon the type of procedure and/or apparatus that was employed. For example, if a method involved use of a solvent, it might extract materials other than oil from the water and therefore such other materials would be defined as oil in an erroneous manner.

Furthermore, even standard procedures for determining oil content in water had various difficulties and drawbacks, among which was the lack of sensitively for determining the presence of oil in low parts per million range. In addition, such procedures have been laboratory types of operation, and as such they are time consuming and non-continuous in the measurements made.

Consequently, it is an object of this invention to provide a method and apparatus for continuously monitoring the presence of oil in water which particularly deals with a procedure involving infrared absorption measurement.

SUMMARY OF THE INVENTION

Briefly, the invention concerns a method of continuously monitoring the presence of oil in water. It comprises the steps of mixing a predetermined proportion of a chemical oil-solvent with said water to form a solution containing any oil therein, and separating said solution from said water. It also comprises flowing said separated solution continuously past a monitor for determining the presence of oil in said solution.

Again briefly, the invention concerns a method of continuously monitoring the presence of oil in water which comprises the steps of mixing about 10 percent by volume of trichlorotrifluoroethane with about 90 percent by volume of said water. The said mixing comprises stirring said mixture at a maximum shear rate without producing a stable emulsion, and circulating said stirred mixture. It also comprises diverting a portion of said stirred mixture. The method also comprises the steps of collecting and settling said diverted portion to separate said trichlorotrifluoroethane solution by gravity, and flowing said separated solution past an absorption cell of an infrared spectrometer employing a wavelength of about 3.4 microns.

Once more briefly, the invention concerns a system for continuously monitoring the presence of oil in water. It comprises in combination a mixing container having an inlet conduit connected thereto for said water to flow therein, and a branch conduit connected to said inlet conduit and adapted for mixing about 10 percent by volume of trichlorotrifluoroethane with said water. It also comprises a stirrer in said mixing container for stirring the mixture at a shear rate less than enough to form a stable emulsion, and a circulating conduit connected to said mixing container for circulating a portion of said stirred mixture. It also comprises a settling container having an overflow outlet near the top and another outlet near the bottom and an inlet between said outlets. It also comprises means for interconnecting said circulating conduit with said settling container inlet, and an infrared spectrometer having means for measuring infrared absorption at a wavelength of about 3.4 microns, and means for interconnecting said settling container outlet near the bottom thereof with said spectrometer for flowing said trichlorotrifluoroethane with oil in solution, to be monitored for absorption at said infrared wavelength of about 3.4 microns.

BRIEF DESCRIPTION OF THE DRAWINGS

The foregoing and other objects and benefits of the invention will be more fully set forth below in connection with the best mode contemplated by the inventors of carrying out the invention and in connection with which there are illustrations provided in the drawings, wherein:

The drawing FIGURE illustrates, in a schematic manner, a system for carrying out the method and/or apparatus in accordance with the invention.

DESCRIPTION OF THE PREFERRED EMBODIMENT

This invention deals with an infrared absorption measuring technique for making a continuous check or monitoring of the oil content in water. Among the advantages of this invention is the fact that there is no problem with calibration because the classes of compounds involved in the oil being detected, all have the same absorptivity. In other words, all crude oils have the same calibration. Furthermore, such calibration can be directly related to a particular synthetic mixture of isooctane, benzene and cetane so that it will conform to a proposed federal standard method of calibrating for such a detecting process.

In addition, the invention has the benefits of an ability to handle silt laden water, since the silt which is in the water being monitored will settle out before and with the solvent solution during the procedure. Also there is no fouling of a measuring cell which is employed to make the infrared absorption measurement, since the procedure involves a chemical solution.

Another advantage is that if the oil content is high, extra oil will be self-purging from the operation of the system.

With reference to the FIGURE of the drawing, it will be observed that there is a mixing container 11 which has an inlet conduit 12 connected thereto. There is also a branch conduit 15 that joins the conduit 12 prior to its connection into the mixing container 11.

The mixing container 11 might take various forms, and for example it may be similar to a commercial motorized blender. Thus, there is a stirring rod 16 that has a paddle tip 19 at the lower end thereof for causing a fluid shearing action as the rod is rotated. The speed of rotation of the mixing rod 16 and its tip 19 is empirically adjusted in order to maintain the shear rate less than that which will create a stable emulsion with the solution being mixed.

The mixing container 11 has a circulating conduit 20 which is connected between an overflow outlet 23 in the container 11, and an inlet 24 near the bottom of the container. Consequently, a body of liquid 27 in the container 11 will tend to circulate through the conduit 20 in a continuous manner.

It will be noted that the conduit 12 is connected to an inlet 28 in the container 11, which is located vertically in between the outlet 23 and inlet 24 of the circulating conduit 20. And, there is a settling container 33 that is connected to receive a portion of the mixture from the circulating conduit 20 via an interconnecting conduit 34.

The settling container 33 has an inlet 37 to which the conduit 34 is connected. The liquid mixture will settle by gravity into an upper portion of water 38, and a lower portion 41 which is an oil-solvent solution that has a greater density than the water.

There is an overflow outlet 42 near the top of the settling container 33. It may have a conduit 43 connected thereto for carrying away overflow water. This would also carry excess oil in the event that the oil quantity become excessive for the amount of solvent. There is another outlet 46 for the solution that is located near the bottom of the settling container 33. A conduit 47 is connected to the outlet 46 for carrying the oil in solvent 41 out from the bottom of the settling container 33 to a cell 48 of an infrared spectrometer 49. Of course, the spectrometer 49 may include a recorder 50 if desired.

There are siphon breaking stand pipes 52 and 53 connected into the high points of the conduits 34 and 47 respectively. These are only schematically indicated since, of course, each must actually extend vertically upward to reach above the highest level of liquid in the connected system.

It will be understood that the spectrometer also includes an infrared detector element 54 that senses the amount of absorption of the infrared energy having a predetermined wavelength which the fluid in the cell 48 absorbs.

Method of Operation

A particular example of a method in accordance with the invention, may be described with reference to the drawing FIGURE. A first step is that of mixing about 10 percent by volume of the oil solvent (trichlorotrifluoroethane) with the water that is being monitored for oil content. Such mixture is accomplish by the pumping rates of water being introduced in the conduit 12, and the solvent flowing through the conduit 15.

It may noted that while the particular solvent trichlorotrifluoroethane is preferred, other solvents may be employed so long as they meet the requirements of forming a chemical solution with any oil in the water and at the same time have a density that is greater than water for effecting the separation later on. Also, the solvent needs to be one which does not have significant infrared absorbency at the infrared wavelength which is employed to detect the presence of oil. It may be noted that carbontetrachloride meets these requirements although it has the disadvantage of being a highly toxic substance.

The mixture of water which is being monitored, and the oil solvent that is being introduced therewith, both flow into the mixing container 11. There they are thoroughly mixed while employing a shear rate that is sufficient to insure thorough mixing in order to obtain a chemical solution of all the oil contained in the water while not being sufficiently high in shear rate to form a stable emulsion between the solution and the water.

One step which helps to obtain the desired results, is that of employing the circulating conduit 20 so that most of the liquid mixture 27 continues to circulate from the mixing chamber 11 around thorough the conduit 20. During the mixing procedure, a portion of the mixture is diverted through the conduit 34 and flows over into the settling container 33.

In the container 33 the liquid constituents are allowed to separate out under gravity action, so that the water 38 floats on top of the oil-solvent solution 41 that collects at the bottom of the container 33. Then, solution 41 is carried through the conduit 47 to the cell 48 of the infrared spectrometer 49 where the absorption reading is taken. The reading involves the infrared detector 54 of the spectrometer.

It will be appreciated that the process is continuous so that whenever any oil appears in the water which is being monitored, it will go into solution with the oil solvent and then following the separation, it will pass through the cell 48 of the spectrometer. The spectrometer will measure an absorption change and provide a reading which indicates the presence of the oil in the oil-solvent solution. It may be noted that this is a highly sensitive procedure and is accurate to indicate very small quantities of oil in the water.

While particular embodiments of the invention have been described above in considerable detail, in accordance with the applicable statutes, this is not to be taken as in any way limiting the invention but merely as being descriptive thereof.

We claim:

1. A system for continuously monitoring the presence of oil in water, comprising in combination
    means for mixing a predetermined proportion of an oil-solvent with said water to form a chemical solution containing any oil therein, comprising means for combining streams of said water and said solvent in said predetermined proportions, and means for stirring said combined streams without producing a stable emulsion, also means for circulating said combined and stirred mixture,
    means for diverting a portion of said circulating mixture,
    a settling container for separating said diverted portion into said solution and said water,
    said solvent does not have significant infrared absorbency at a predetermined infrared wavelength and has a different density from said water,
    an infrared spectrometer for determining the presence of oil in said solution, and
    means for flowing said separated solution past said infrared spectrometer.

2. A system according to claim 1, wherein said infrared spectrometer comprises means for measuring absorbency at said predetermined wavelength.

3. A system for continuously monitoring the presence of oil in water, comprising in combination
    a mixing container having an inlet conduit connected thereto for said water to flow therein,
    a branch conduit connected to said inlet conduit and adapted for mixing about ten percent by volume of trichlorotrifluoroethane with said water,
    a stirrer in said mixing container for stirring the mixture at a shear rate less than enough to form a stable emulsion,
    a circulating conduit connected to said mixing container for circulating a portion of said stirred mixture, a settling container having an overflow outlet near the top and another outlet near the bottom of an inlet between said outlets, means for interconnecting said circulating conduit with said settling container inlet, an infrared spectrometer having means for measuring infrared absorption at a wavelength of about 3.4 microns, and means for interconnecting said settling container outlet near the bottom thereof with said spectrometer for flowing said trichlorotrifluoroethane with oil in solution to be monitored for absorbency at said infrared wavelength of about 3.4 microns.

4. Method of continuously monitoring the presence of oil in water, comprising the steps of mixing about ten percent by volume of trichlorotrifluoroethane with about ninty percent by volume of said water, said mixture comprising stirring said mixture at a maximum shear rate without producing a stable emulsion, circulating said stirred mixture, and diverting a portion of said stirred mixture, collecting and settling said diverted portion to separate said trichlorotrifluoroethane solution by gravity, and flowing said separated solution past an absorption cell of an infrared spectrometer employing a wavelength of about 3.4 microns.

5. Method of continuously monitoring the presence of oil in water, comprising the steps of mixing a predetermined proportion of a chemical oil-solvent with said water by stirring a combined stream of said water and said oil-solvent without producing a stable emulsion, said solvent having a different density from said water, circulating said stirred mixture while diverting a portion thereof, separating said solution from said water by permitting said diverted portion of stirred mixture to settle, said solvent having no significant infrared absorbency at a predetermined infrared wavelength, and flowing said separate solution continuously past an infrared spectrometer for determining the presence of oil in said solution.

6. Method according to claim 5, wherein said infrared spectrometer measures absorbency at said predetermined infrared wavelength.

7. Method according to claim 6, wherein said solvent is trichlorotrifluoroethane, and said predetermined infrared wavelength is about 3.4 microns.

8. Method according to claim 6, wherein said solvent is carbon tetrachloride, and said predetermined infrared wavelength is about 3.4 microns.

* * * * *

UNITED STATES PATENT AND TRADEMARK OFFICE
CERTIFICATE OF CORRECTION

PATENT NO. : 4,045,671
DATED : August 30, 1977
INVENTOR(S) : R. M. DILLE et al

It is certified that error appears in the above-identified patent and that said Letters Patent are hereby corrected as shown below:

Column 3, line 19, "become" should read --became--.

Column 5, line 2, "of" should read --and--.

Signed and Sealed this

Twenty-second Day of August 1978

[SEAL]

Attest:

RUTH C. MASON
Attesting Officer

DONALD W. BANNER
Commissioner of Patents and Trademarks